(12) United States Patent
Camacho et al.

(10) Patent No.: US 9,011,409 B2
(45) Date of Patent: Apr. 21, 2015

(54) NON-CORING FILL NEEDLE

(76) Inventors: Victor Camacho, Santa Clarita, CA (US); Roberto Rosillo, Van Nuys, CA (US); James Coates, Sun Valley, CA (US); Stephen Kurtin, Sherman Oaks, CA (US)

( * ) Notice: Subject to any disclaimer, the term of this patent is extended or adjusted under 35 U.S.C. 154(b) by 393 days.

(21) Appl. No.: 13/396,019

(22) Filed: Feb. 14, 2012

(65) Prior Publication Data

US 2012/0215197 A1 Aug. 23, 2012

Related U.S. Application Data

(60) Provisional application No. 61/463,716, filed on Feb. 22, 2011.

(51) Int. Cl.
*A61M 5/32* (2006.01)
*A61M 5/178* (2006.01)

(52) U.S. Cl.
CPC .............. *A61M 5/3286* (2013.01); *A61M 5/178* (2013.01); *A61M 5/3291* (2013.01); *A61M 2205/195* (2013.01)

(58) Field of Classification Search
CPC ............... A61B 17/32; A61B 17/3205; A61B 17/32053; A61B 17/34; A61B 17/3417; A61B 17/3474; A61B 17/349; A61B 17/3496; A61B 2017/1107; A61B 2017/1135; A61B 2017/349; A61B 2019/481; A61B 17/04; A61B 17/06; A61J 1/10; A61J 1/20; A61J 1/208; A61J 1/2089; A61J 1/2096; A61J 2001/201; A61J 2001/2055; A61J 2001/2075; A61M 5/162; A61M 5/1626; A61M 5/32; A61M 5/3202; A61M 5/3213; A61M 5/3216; A61M 5/3243; A61M 5/326
USPC ............ 604/184, 185, 192, 411, 414; 222/80, 222/81, 83, 85
See application file for complete search history.

(56) References Cited

U.S. PATENT DOCUMENTS

| | | |
|---|---|---|
| 207,551 A | 8/1878 | Rodgers |
| 806,746 A | 12/1905 | Miller |
| 1,192,596 A | 7/1916 | Albrecht |
| 5,925,834 A * | 7/1999 | Sgourakes .................. 73/864.11 |
| 7,131,951 B2 * | 11/2006 | Angel ............................ 600/567 |
| 8,512,307 B2 * | 8/2013 | Fangrow ....................... 604/411 |

\* cited by examiner

*Primary Examiner* — Melanie Hand
(74) *Attorney, Agent, or Firm* — Saul Epstein

(57) ABSTRACT

A non-coring needle that includes a sharpened and hardened tip having a tapered back region against which a length of tubing is pressed and welded, brazed or soldered. A Luer Lock hub may be attached to the other end of the tubing.

8 Claims, 2 Drawing Sheets

NON-CORING FILL NEEDLE

RELATED APPLICATIONS

This application claims the benefit under 35 USC §119(e) of the filing date of U.S. Provisional Patent Application No. 61/463,716 entitled "Non-Coring Fill Needle", filed Feb. 22, 2011.

BACKGROUND OF THE INVENTION

One method of filling a volume with liquid involves the use of a pointed fill needle that is attached to a syringe containing the liquid to be injected, piercing a wall of the volume with the needle, and pumping the liquid from the syringe into the volume. In order to accommodate this method, the wall of the volume is fitted with a rubber or rubber-like fill area that can be pierced by the needle. Ideally, when the needle is removed after the fill step, the rubber closes around the puncture, sealing the opening. In order for the fill area to be leak free, the needle must be of a "non-coring" type. And also, the surface of the needle must be smooth in order to prevent tearing of the rubber that could provide a path for liquid to escape. Depending on the tear characteristics of the rubber, and its dimensions at the fill area, the fill needle may have to be relatively small, in many cases less than one millimeter in diameter, to avoid post-fill leakage.

SUMMARY OF THE INVENTION

For convenience, the present invention is described in connection with a needle having a conventional "Luer-Lock" hub that can be attached to standard syringes. Other styles of connection to the filling needle, of course, are also possible. The needle tubing may be held in the hub by soldering, swaging, adhesives, or other common means. The free end of the needle is closed with a sharp pointed solid tip to facilitate a "non-coring" piercing of the wall of the volume to be filled. A cross hole near the tip end of the needle allows the filling liquid to be transferred from the syringe to the volume. The crux of the invention resides in the design of the tip that closes the end of the tubing, and how it is fastened to the tubing.

The tip is preferably machined from hardenable stainless steel that is preferably subsequently hardened, and has a tapered sharp end for piercing the rubber fill area of the volume to be filled. While it is not practically possible to make and maintain an absolutely sharp tip, reasonable sharpness is required in order to penetrate the wall of the fill area without tearing that wall. Behind the sharp end of the tip, i.e., at the back of the tip, is a region of the tip having a reverse taper against which the needle tubing is pressed and laser welded. The tapered fit-up between the tubing and the tip assures concentricity and metal-to-metal contact, independent of any tolerances, while enabling a very short dimension from the cross hole to the tip. It also enables co-linear alignment of the tip with the tubing. The tip OD is preferably larger than the tubing OD so as to provide a "shadowing" effect for the weld, whereby rubbing of the rubber against the weld joint is minimized.

DETAILED DESCRIPTION OF THE INVENTION

Figure 1:
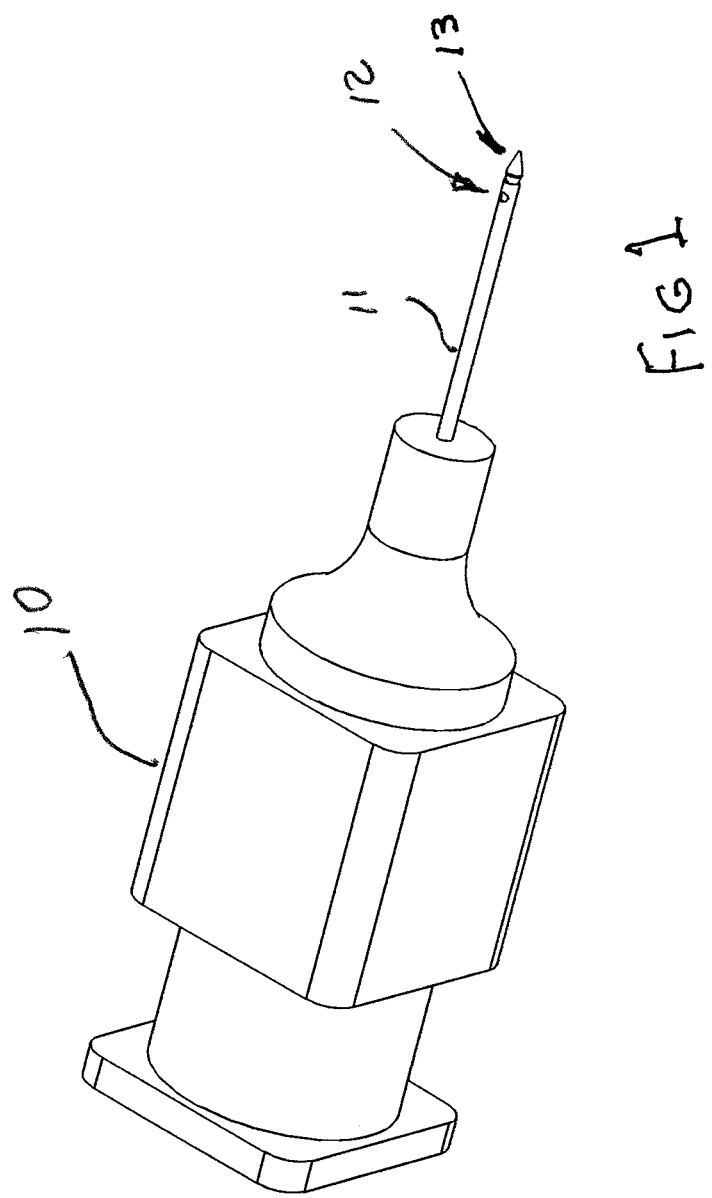
FIG. 1 is a trimetric view of a completed fill needle according to the invention.

FIG. 1 shows a completed fill needle according to the invention having a "Luer-Lock" hub 10 into which needle tubing 11 is inserted and held by conventional means, such as soldering. In use, the hub can be attached to standard syringes that contain the liquid to be injected. The needle tubing diameter depends on the particular application. While there is no limitation on needle diameter, the invention is particularly adapted to applications involving sub-millimeter diameter needles. A cross hole 12 in the tubing through at least one wall near the tip provides an exit aperture for the liquid to be injected. Preferably, the cross hole goes through both walls.

Figure 2:
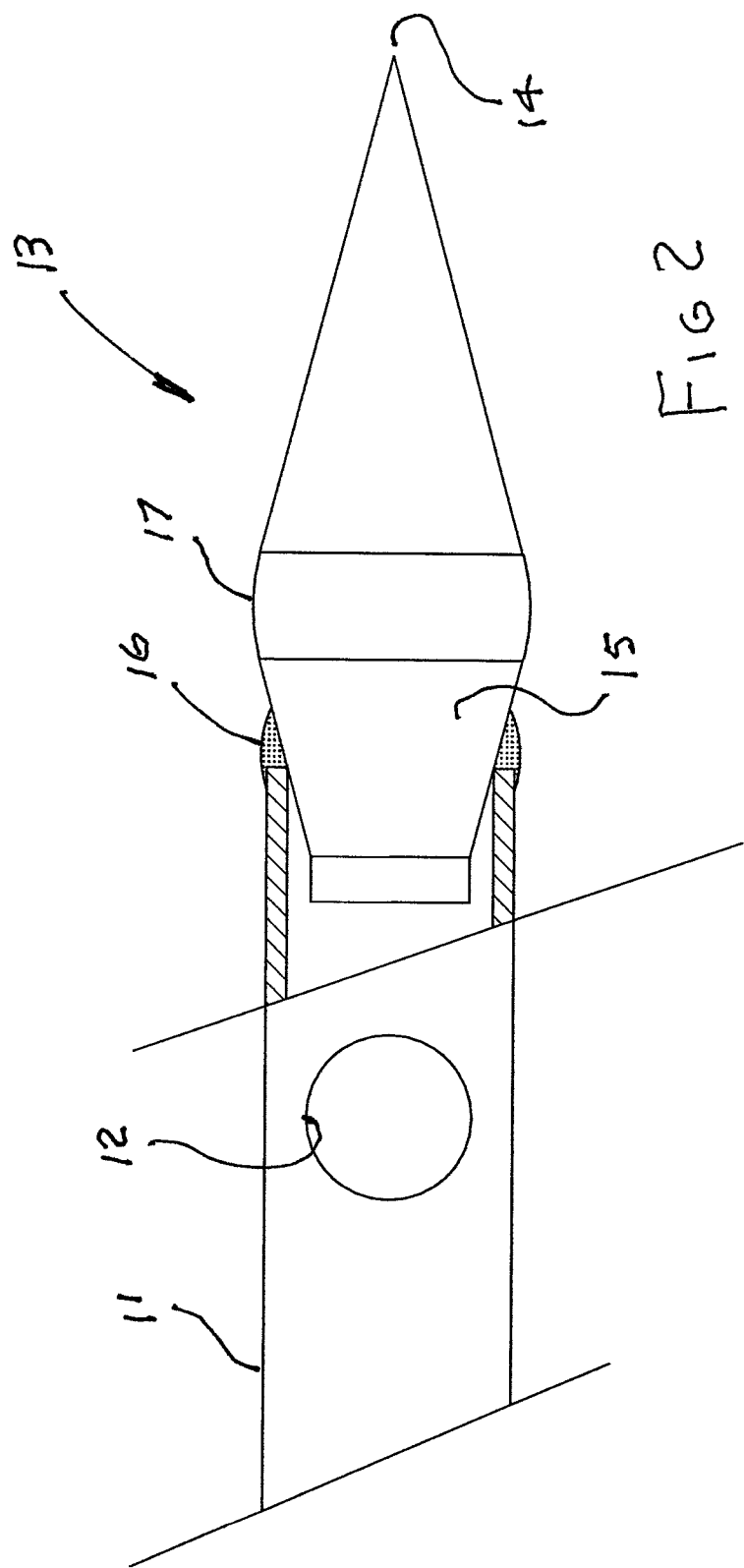
FIG. 2 is a partially sectioned side view of the needle tubing and tip portion of a fill needle according to the invention. Note that the weld shown is not an accurate representation of a finished weld. The drawing is intended to illustrate the position of the tubing with respect to the tip before welding, and the location of the weld. The Figure does not depict the precise interface between the weld melt and the unmelted portions of the tubing and tip.

FIG. 2 shows a partially sectioned side view of the needle tubing and tip portion of a fill needle. Tip 13, attached to the end of the tubing as will be discussed below, tapers to a sharp point 14. The point facilitates piercing of the wall through which the fill liquid is to be injected, without tearing. The steepness of the tapered end is not critical, but the tip should be sharp enough to facilitate easy piercing of the wall of the fill area. Behind the front taper is a region of reverse taper 15 against which the end of tubing 11 rests. During fabrication, the tip 13 is pushed against the end of tubing 11, the tip aligned co-linearly with the tubing, and the two parts are preferably laser welded together using a multiplicity of weld spots (16) around the circumference. The weld is preferably made without filler, but filler can be used if desired. It is preferred that the weld spots form a continuous seam, so as to avoid portions of the sharp tubing end to remain exposed. Care should be taken to achieve a smooth weld so that tearing of the rubber on insertion, or withdrawal, of the needle is avoided. The weld joint can be subsequently smoothed, if desired. As an alternative to welding, other heat activated methods of joining the tip to the tubing may be used, such as brazing and soldering, including silver solder. The OD 17 of the tip is preferably made larger than the OD of the tubing so that there is minimal rubbing against the weld spots of the rubber fill wall through which the needle is inserted. Also, preferably, the weld (or solder or braze) does not extend radially at any point beyond the outer circumference of the tip so that the tip "shadows" the possibly less than perfectly smooth weld.

We claim:

1. A non-coring needle which comprises:
   a metal tip that has a front portion and a back portion, said front portion being tapered toward a sharpened end and said back portion having a reverse taper;
   a length of metallic tubing abutting said reverse tapered back portion, said tubing and said reverse tapered back portion of said tip being joined by welding, brazing or soldering; and
   a cross-hole through at least one wall of said tubing near the said tip.

2. A non-coring needle as recited in claim 1 where said tip is cylindrical and the maximum outside diameter of said tip is larger than the outside diameter of said tubing.

3. A non-coring needle as recited in claim 2 wherein said length of tubing has a central axis and the outer diameter of said weld, braze or solder is less than the outer diameter of said tip.

4. A non-coring needle as recited in claim 1 wherein said cross-hole passes through both sides of said tubing.

5. A non-coring needle as recited in claim 1 and further including a hub attached to said tubing at the end opposite said tip.

6. A non-coring needle as recited in claim 4 where said hub is of the Luer-Lock type.

7. A non-coring needle as recited in claim 1 where said tip has been hardened.

8. A non-coring needle as recited in claim 1 wherein said welding is accomplished without filler.

* * * * *